United States Patent
Laby et al.

(10) Patent No.: US 9,737,198 B2
(45) Date of Patent: Aug. 22, 2017

(54) SYSTEM FOR CONTROLLING AN INSTRUMENT USING SHAPE SENSORS

(71) Applicant: INTUITIVE SURGICAL OPERATIONS, INC., Sunnyvale, CA (US)

(72) Inventors: Keith P. Laby, San Francisco, CA (US); Robert M. Ohline, Redwood City, CA (US); Christoph M. Pistor, Mountain View, CA (US); Charles E. Swinehart, San Jose, CA (US); Bruce R. Woodley, Palo Alto, CA (US); Amir Belson, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/303,270

(22) Filed: Jun. 12, 2014

(65) Prior Publication Data
US 2014/0330080 A1    Nov. 6, 2014

Related U.S. Application Data

(63) Continuation of application No. 12/524,249, filed as application No. PCT/US2008/052365 on Jan. 29, 2008, now Pat. No. 8,784,303.
(Continued)

(51) Int. Cl.
*A61B 1/00* (2006.01)
*A61B 1/04* (2006.01)
(Continued)

(52) U.S. Cl.
CPC ........ *A61B 1/0055* (2013.01); *A61B 1/00045* (2013.01); *A61B 1/0052* (2013.01);
(Continued)

(58) Field of Classification Search
CPC ............ A61B 19/5244; A61B 19/5212; A61B 19/5217; A61B 2019/5246;
(Continued)

(56) References Cited

U.S. PATENT DOCUMENTS

| 4,930,494 A | 6/1990 | Takehana et al. |
| 5,633,494 A | 5/1997 | Danisch |

(Continued)

FOREIGN PATENT DOCUMENTS

| JP | H0245702 U | 3/1990 |
| JP | H0380825 A | 4/1991 |

(Continued)

OTHER PUBLICATIONS

English Language Translation of Office Action dated Apr. 1, 2013 for Japanese Application No. 2009547471 filed Jan. 29, 2008.
(Continued)

*Primary Examiner* — Anhtuan T Nguyen
*Assistant Examiner* — William Chou

(57) ABSTRACT

The present invention relates, generally, to controlling a steerable instrument having an elongate body. More particularly, the present invention relates to a system and method for sensing the shape of a steerable instrument and controlling the steerable instrument in response to a control signal from a user input device and a shape signal corresponding to the sensed shape of at least a portion of the steerable instrument. The present invention also relates to a system for sensing the shape of a flexible instrument with an optical shape sensor.

25 Claims, 5 Drawing Sheets

Related U.S. Application Data

(60) Provisional application No. 60/898,200, filed on Jan. 29, 2007.

(51) Int. Cl.
*A61B 1/005* (2006.01)
*A61B 1/05* (2006.01)
*A61B 1/313* (2006.01)
*A61B 34/20* (2016.01)

(52) U.S. Cl.
CPC ............... *A61B 1/05* (2013.01); *A61B 1/313* (2013.01); *A61B 2034/2061* (2016.02)

(58) Field of Classification Search
CPC .... A61B 2019/5261; A61B 2019/5259; A61B 1/00147; A61B 1/00149; A61B 1/0016; A61B 1/005; A61B 1/0051; A61B 1/0052; A61B 1/0053; A61B 1/0055; A61B 1/0056; A61B 1/0057
USPC ........ 600/117, 139, 141, 145, 146, 149, 587
See application file for complete search history.

(56) References Cited

U.S. PATENT DOCUMENTS

| | | | |
|---|---|---|---|
| 5,728,044 A | 3/1998 | Shan | |
| 5,957,833 A | 9/1999 | Shan | |
| 6,389,187 B1* | 5/2002 | Greenaway | G01M 11/083 385/13 |
| 6,563,107 B2 | 5/2003 | Danisch et al. | |
| 6,845,190 B1 | 1/2005 | Smithwick et al. | |
| 8,784,303 B2 | 7/2014 | Laby et al. | |
| 2002/0183592 A1 | 12/2002 | Suzuki et al. | |
| 2004/0165810 A1 | 8/2004 | Fujita | |
| 2006/0013523 A1 | 1/2006 | Childlers et al. | |
| 2007/0142749 A1 | 6/2007 | Khatib et al. | |
| 2007/0156019 A1 | 7/2007 | Larkin et al. | |
| 2008/0097159 A1 | 4/2008 | Ishiguro | |
| 2008/0212082 A1* | 9/2008 | Froggatt | G01M 11/083 356/73.1 |
| 2010/0099951 A1 | 4/2010 | Laby et al. | |

FOREIGN PATENT DOCUMENTS

| | | |
|---|---|---|
| JP | H04146716 A | 5/1992 |
| JP | H0556910 A | 3/1993 |
| JP | H05176879 A | 7/1993 |
| JP | H05285091 A | 11/1993 |
| JP | H07234346 A | 9/1995 |
| JP | 2000258190 A | 9/2000 |
| JP | 2001133584 A | 5/2001 |
| JP | 2001169998 A | 6/2001 |
| JP | 2001289617 A | 10/2001 |
| JP | 2003185897 A | 7/2003 |
| JP | 2003225195 A | 8/2003 |
| JP | 2004251779 A | 9/2004 |
| JP | 2004358095 A | 12/2004 |
| JP | 2005319325 A | 11/2005 |
| JP | 2006314775 A | 11/2006 |
| JP | 2007130174 A | 5/2007 |
| WO | WO-9933392 A1 | 7/1999 |
| WO | WO-2004019769 A1 | 3/2004 |
| WO | WO-2005084542 A1 | 9/2005 |
| WO | WO-2006134881 A1 | 12/2006 |
| WO | WO-2008094949 A2 | 8/2008 |

OTHER PUBLICATIONS

English Language Translation of Office Action dated Nov. 29, 2012 for Japanese Application No. 2009547471 filed Jan. 29, 2008.
International Search Report for Application No. PCT/US2008/052365, dated Sep. 19, 2008, 5 pages.
PCT/US08/52365 International Preliminary Report on Patentability, dated Aug. 4, 2009, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Written Opinion for Application No. PCT/US2008/052365, 9 pages.
Notification of the Office Action for related Japanese Application No. 2015-019883, dated Jan. 5, 2016.

* cited by examiner

SYSTEM FOR CONTROLLING AN INSTRUMENT USING SHAPE SENSORS

CROSS-REFERENCE TO RELATED APPLICATIONS

This application is a continuation application of U.S. patent application Ser. No. 12/524,249 (filed Jul. 23, 2009), which is a national stage application of International Application No. PCT/US2008/052365 (filed Jan. 29, 2008), which claims the benefit of priority of U.S. Provisional Patent Application No. 60/898,200 (filed Jan. 29, 2007), which are all incorporated herein by reference in their entirety.

INCORPORATION BY REFERENCE

All patents, patent publications and patent applications mentioned in this application are incorporated herein, in their entirety, by reference to the same extent as if each individual publication or patent application was specifically and individually indicated to be incorporated by reference.

FIELD OF THE INVENTION

The present invention relates, generally, to articulating instruments or snake-like robots. More particularly, the present invention relates to sensing the shape of articulating instruments or snake-like robots.

BACKGROUND OF THE INVENTION

Endoscopes, colonoscopes and other controllable instruments have found widespread medical and industrial uses. As the complexity of the movement or use of such instruments increases, there is a need to more precisely control, locate within the body or identify the shape of the controllable instrument. A number of different types of shape sensing devices are available.

While shape sensing devices are available, challenges remain in the integration of shape sensing devices into controllable instruments. Challenges remain in systems capable of coordinated use of the shape information for control or operation of the controllable instrument or procedures that would benefit from shape information. Embodiments of the inventive systems and controllable instruments described herein address these and other challenges.

SUMMARY OF THE INVENTION

One aspect of the invention provides an instrument having an elongate body, comprising a steerable distal portion and a plurality of articulating segments. The instrument can be modified to incorporate a shape sensor to indicate the shape of at least a portion of the instrument. In one embodiment, the shape sensor is an optical shape sensor. In other embodiments, the shape sensor can be a resistance changing flexible band, a bend sensor, a potentiometer, or a magnetic sensor, for example.

Another aspect of the invention provides a system that closes the control loop between the control signals used to direct the movement of an instrument and the shape indicating signal for the shape of all or a portion of the instrument. The system can comprise a user input device, a controller, an instrument having articulating segments, and a shape sensor, for example. The controller is configured to direct the movement of the instrument in response to a control signal from the user input device and a shape signal from the shape sensor.

Yet another aspect of the invention provides a method of controlling an instrument having an elongate body. The method includes the steps of inputting a control signal to a controller to change the shape of an instrument; sensing the shape of a portion of the instrument with a shape sensor; outputting a shape signal corresponding to the shape of the portion of the instrument from the shape sensor to the controller; and directing the movement of the instrument in response to the control signal and the shape signal.

One aspect of the invention provides a system for sensing the shape of an instrument. The system comprises an instrument having an elongate body, a shape sensor extending along a portion of the elongate body in a spiral pattern, and an indicator on each end of the shape sensor to maintain the axial orientation of the ends of the shape sensor. The spiral pattern can comprise an integral number of full spiral turns from one end of the elongate body to the other end. In one embodiment, the shape sensor is an optical shape sensor. The axial orientation of the shape sensor can be maintained in a variety of ways, including, but not limited to, physical or visual markers on the shape sensor, clipping the shape sensor to the elongate body, or integrating the shape sensor into the elongate body.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
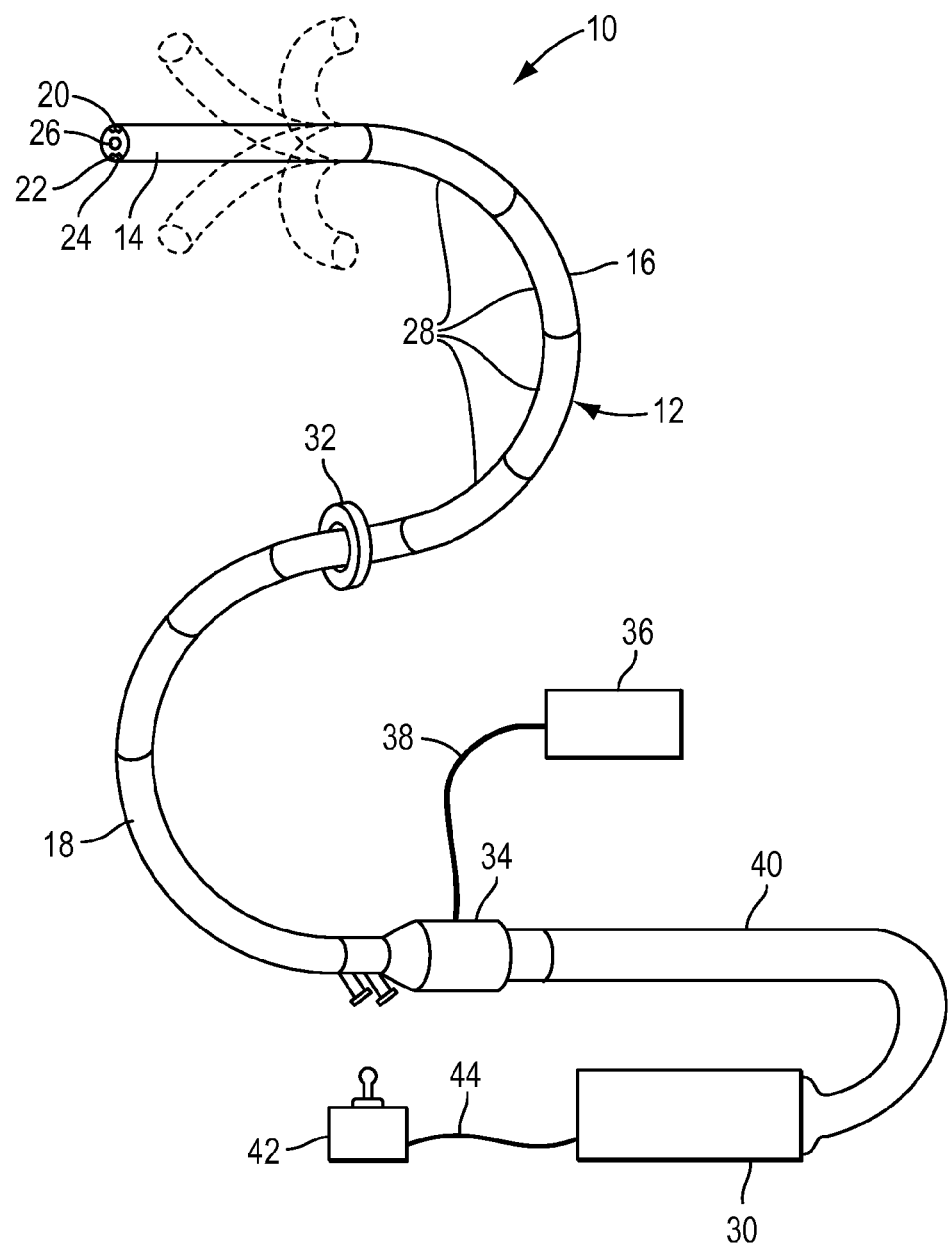
FIG. 1 illustrates a steerable endoscope in accordance with one embodiment of the present invention.
Figure 3:
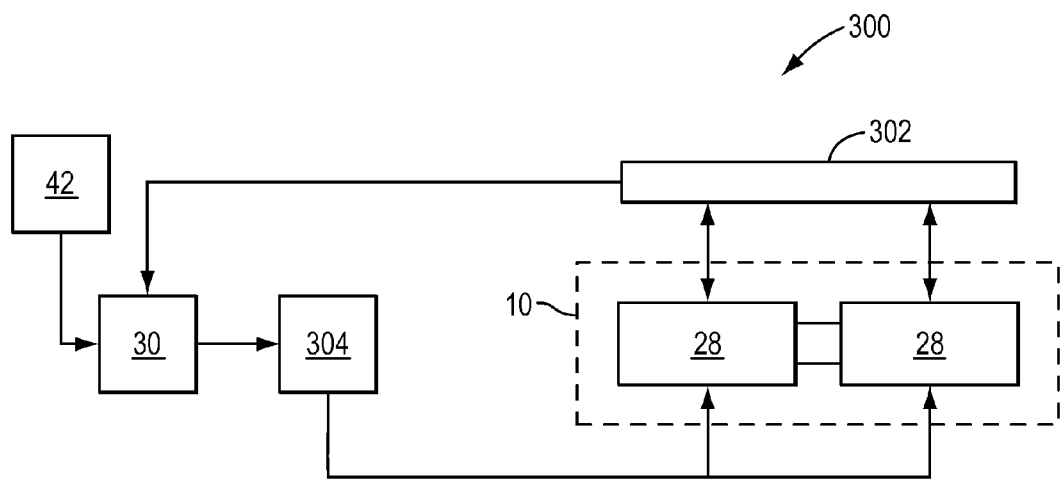
FIG. 3 illustrates a system that closes the control loop between control signals used to direct the movement of a controllable instrument and a shape indicating signal for the shape of all or a portion of the controllable instrument in accordance with an embodiment of the present invention.

FIG. 1 depicts an instrument 10, in accordance with an embodiment of the present invention. Instrument 10 has elongate body 12 with steerable distal portion 14, automatically controlled proximal portion 16, and flexible and passively manipulated proximal portion 18. Automatically controlled proximal portion 16 may also be flexible and passively manipulated, although it is preferred to provide automatically controlled proximal portion 16. Elongate body 12 can have only steerable distal portion 14 and automatically controlled portion 16. As described below and as schematically illustrated in FIG. 3, the instrument 10 and the associated control system or controller may be modified to incorporate a shape sensor and control the instrument based at least in part on a shape indicating signal provided by one or more shape sensors on or associated with the instrument 10. Fiber optic imaging bundle 20 and illumination fiber(s) 22 may extend through elongate body 12 to steerable distal portion 14, or video camera 24 (e.g., CCD or CMOS camera) may be positioned at the distal end of steerable distal portion 14. A user views live or delayed video feed from video camera 24 via a video cable (e.g., wire or optical fiber, not shown) or through wireless transmission of the video signal. Typically, instrument 10 will also include one or more access lumens, working channels, light channels, air and water channels, vacuum channels, and a host of other well known complements useful for both medical and industrial endoscopy. These channels and other amenities are shown generically as working channel 26. In particular these amenities may include multiple tool channels in order to provide access for tools to a surgical site by passing the instrument through a natural orifice proximate to a surgical target site, as in natural orifice transluminal (or transgastric) endoscopic surgery (NOTES). Various details of the use of a controllable instrument and methods for using a controllable instrument in a transluminal or NOTES procedure are further described in U.S. patent application Ser. No. 11/522,305 titled "Methods and Apparatus for Performing Transluminal and Other Procedures," filed on Sep. 14, 2006 and commonly assigned to the assignee of the present application. The systems, instruments and devices described in "Methods and Apparatus for Performing Transluminal and Other Procedures" may be modified as described herein to provide shape sensing capabilities and/or control to the systems, instruments and methods described therein.

Preferably, automatically controlled proximal portion 16 comprises a plurality of articulating segments 28, which are controlled via computer and/or electronic controller 30. Such an automatically controlled endoscope is described in further detail in commonly assigned U.S. patent application Ser. No. 10/229,577, now U.S. Pat. No. 6,858,005, titled "Tendon-Driven Endoscope and Methods of Insertion," filed on Aug. 27, 2002, and U.S. patent application Ser. No. 11/750,988 titled "Methods and Apparatus for Displaying Three-Dimensional Orientation of a Steerable Distal Tip of an Endoscope," filed on May 18, 2007, both commonly assigned to the assignee of the present application. Preferably, the distal end of a tendon is mechanically connected to each articulating segment 28 or steerable distal portion 14, with the proximal end of the tendon mechanically connected to actuators to move articulating segments 28 or steerable distal portion 14. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they can be configured into several wire bundles attached at a proximal end of each of the tendons within the actuator. The actuators driving the tendons may be positioned inside instrument 10, or, alternatively, the actuators may be positioned outside instrument 10.

Segment articulation may be accomplished by applying energy, e.g., electrical current, electrical voltage, heat, etc., to each of the bundles to actuate a linear motion in the wire bundles which in turn actuate the tendon movement. The linear translation of the actuators within the controller may be configured to move over a relatively short distance to accomplish effective articulation depending upon the desired degree of segment movement and articulation. In one embodiment, knobs attached to rack and pinion gearing can be used to actuate the tendons attached to steerable distal portion 14. An axial motion transducer 32 (also called a depth referencing device or datum) may be provided for measuring the axial motion, i.e., the depth change, of elongate body 12 as it is advanced and withdrawn. As elongate body 12 of instrument 10 slides through axial motion transducer 32, it indicates the axial position of the elongate body 12 with respect to a fixed point of reference. Axial motion transducer 32 is more fully described in U.S. patent application Ser. No. 11/522,305 titled "Methods and Apparatus for Performing Transluminal and Other Procedures," filed on Sep. 14, 2006. Additionally, an optical sensor may be used to determine the axial position of the instrument, either alone or in combination with an optical shape sensor as more fully described below. In either case, the depth information combined with the shape information can be used to construct a three-dimensional image of the elongate body as it is inserted or withdrawn. Additionally, information from such a system may be used to provide, the shape of the pathway followed by the sensor from a reference point (i.e., the datum). Additionally, information from such a system may be used as input to a control system to: (i) Drive the instrument to a location under the control of a user; (ii) Provide recommended steering commands to a user to manipulate the instrument to a desired location or orientation (iii) Automatically control the instrument to conform to inputs from a user, a predetermined pathway (surgical planning) or inputs from an imaging system or display.

In the embodiment depicted in FIG. 1, handle 34 is connected to illumination source 36 by illumination cable 38 that is connected to or continuous with illumination fibers 22. Handle 34 is connected to electronic controller 30 by way of controller cable 40. User input device 42 (e.g., a joy stick) is connected to electronic controller 30 by way of second cable 44 or directly to handle 34. Controller 30 controls the movement of the segmented automatically controlled proximal portion 16.

Figure 2A:
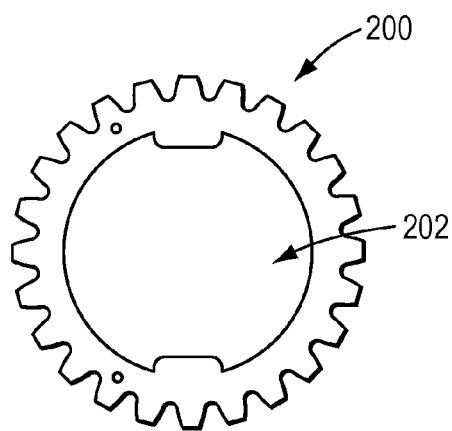
FIGS. 2A-2C depict embodiments of vertebrae-type links in accordance with an embodiment of the present invention.
Figure 2B:
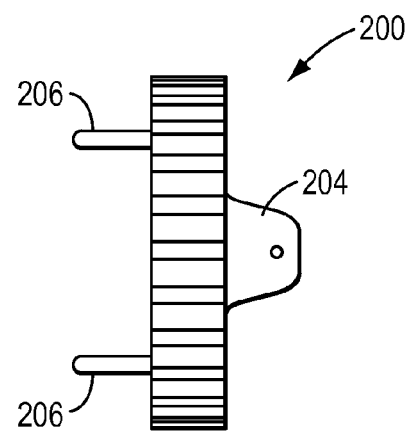
Figure 2C:
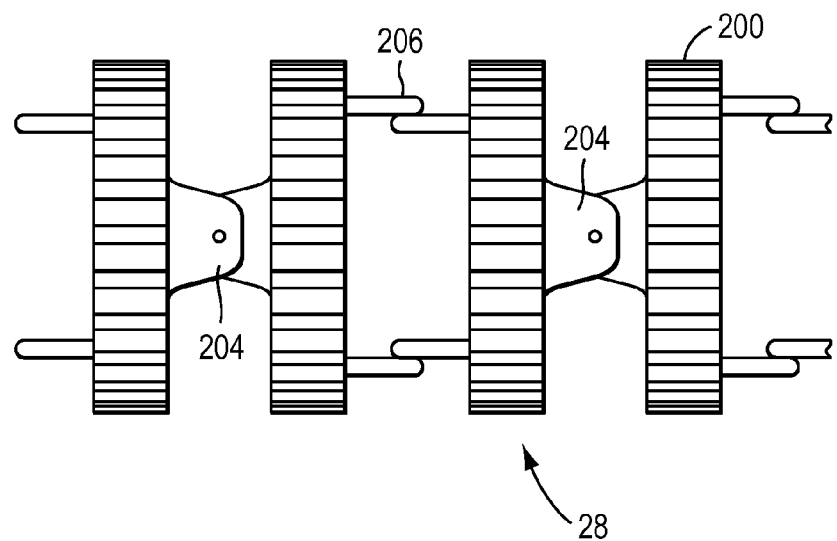

In one embodiment, articulating segments 28 of instrument 10 can be constructed from a plurality of links 200 as shown in FIGS. 2A-2C. FIG. 2A shows an end view of a single link 200. Each link 200 can define a central aperture or working channel 202 that can collectively form the internal lumen as previously described. As shown in FIG. 2B, the links 200 may have two pairs of hinges 204 and 206. The first pair of hinges 204 can project perpendicularly from a first face of link 200 and a second pair of hinges 206 located 90 degrees around the circumference from the first pair, projecting perpendicularly away from the face of link 200 on a second face of the vertebra opposite to the first face. In the embodiment shown in FIG. 2C, each articulating segment 28 can comprise four links 200, although any number of links may be used including just one link. The ultimate number of links 200 used is primarily defined by the purpose for which articulating segments 28 or instrument 10 will be used. Each link 200, in this embodiment, can move with one degree of freedom relative to an adjacent link. Multiple links provide a segment 28 with two degrees of freedom. Further details of the articulating segments can be found in U.S. patent application Ser. No. 11/871,104 titled "System for Managing Bowden Cables in Articulating Instruments," filed on Oct. 11, 2007 and commonly assigned to the assignee of the present application.

FIG. 3 illustrates an exemplary system 300 and method that closes the control loop between the control signals used to direct the movement of the instrument and a shape indicating signal for the shape of all or a portion of a controllable instrument. The following description of system 300 includes references to instrument 10 of FIG. 1, since the system 300 is implemented utilizing an instrument such as instrument 10. In order to determine the shape of elongate body 12, instrument 10 can further include shape sensor 302 in contact with elongate body 12. For example, the shape sensor can be an optical sensing fiber or fiber bundle extending along the length of the elongate body. Embodiments of the present invention build upon the concept of measuring the shape of the optical fiber and using those measurements to determine curvature and/or relative position of an instrument to which the optical fiber is associated. In some embodiments, shape sensing is accomplished by creating a linear array of high spatial resolution fiber optic bend sensors. In general, by assuming each element is sufficiently small, by knowing the curvature of the structure at each individual element the overall shape is reconstructed through an integration process. Additional types of shape sensors and their orientation on or within instrument 10 will be discussed below in more detail.

In addition to shape sensor 302, system 300 of FIG. 3 also includes user input device 42, controller 30, actuator 304, and articulating segments 28. As previously described, user input device 42 is in communication with controller 30 and is configured to provide a control signal to change the shape of at least one of the articulating segments 28. Controller 30 is in communication with actuator 304 to direct the movement of articulating segments 28 and, thus, control the shape of elongate body 12. In particular, a user inputs a control signal into user input device 42 (i.e., such as a joystick or a computer) which then transmits the control signal to the controller 30. The user may control the instrument 10 or indicate desired motions in several exemplary ways. In one embodiment, the user steers the steerable distal portion 14 with user input device 42 and identifies the direction instrument 10 needs to proceed. Instrument 10 is then advanced and the segments following steerable distal portion 14 take on the shape of the segment before it. This follow-the-leader shape determination, in general, works by proximately adjacent segments taking on the shape of an adjacent distal segment as instrument 10 is advanced distally. The determination as to the degree a segment has conformed to the shape of another segment and the determination of the shape of one or more segments are determined at least in part by a shape sensor. The follow-the-leader shape determination works the same whether advancing distally or withdrawing proximally. Alternatively, in another embodiment, the user can enter any desired shape of the elongate body (i.e., such as into a computer, interacting with a visual display or graphical user interface), irrespective of the steerable distal portion and even without advancement or withdrawal of elongate body 12. In other words, the controller, with or without input from a user, can manipulate the elongate body 12 into any desired shape. The determination as to whether or to what degree the elongate body 12 has moved into the desired shape depends at least in part on a shape indicating signal produced by a shape sensor in communication with the elongate body 12 and the controller 30.

As the shape of instrument 10 changes in response to the control signal from user input device 42, shape sensor 302 provides a shape signal corresponding to the shape of at least one of articulating segments 28. For example, if shape sensor 302 runs along the entire length of elongate body 12, then the shape signal can correspond to the shape of the entire length of elongate body 12. However, for applications where instrument 10 is inserted into a patient, it can be understood that shape sensor 302 need not run along the entire length of elongate body 12, but rather, only be sufficiently long to indicate the shape of the portion of elongate body 12 inserted into a patient (i.e., the portion of elongate body 12 out of sight from the user).

Shape sensor 302 is configured to provide a shape signal corresponding to the shape of at least one of the articulating segments 28. Controller 30, being in communication with both user input device 42 and shape sensor 302, can direct the movement of at least one of the articulating segments 28 in response to the control signal from user input device 42 and the shape signal from shape sensor 302. It can be appreciated that an articulating instrument or snake-like robot as described above may not always achieve the shape intended by the user. For example, an actuator may fail, or the tendons responsible for moving articulating segments 28 may bind, stretch, slip, or break, causing articulating segments 28 to fail to achieve the shape intended by the user. As such, controller 30 can direct the movement of instrument 10 in response to the shape signal from shape sensor 302 to compensate for any errors within instrument 10 so that instrument 10 can automatically achieve the shape intended by the user.

In one embodiment, a user may guide or steer instrument 10 with user input device 42 while monitoring the actual shape of elongate body 12, as sensed by shape sensor 302. For example, system 300 can further include a video display (not shown in FIG. 3) configured to receive the shape signal from shape sensor 302 and display an output representing the shape of a portion of elongate body 12. Thus, the user can guide, steer or direct movement or alteration of the shape of the instrument 10 by monitoring the shape of elongate body 12 as it is displayed on the video display. Since controller 30 directs the movement of elongate body 12 in response to the control signal from user input device 42 and the shape signal from shape sensor 302, system 300 provides a closed-loop feedback control system for controlling instrument 10 in response to the actual shape of the elongate body 12.

In yet another embodiment of system 300, the user can input a desired shape onto an interactive display such as a graphical user interface display or the like and controller 30 can direct instrument 10 to automatically achieve the desired shape. This is accomplished in a similar fashion as described above, as controller 30 directs the movement of elongate body 12 in response to the shape signal from shape sensor 302 until the shape of elongate body 12 matches the desired shape from the user.

System 300 can be implemented in a variety of surgical procedures. For example, a surgical opening can be created in a patient into which instrument 10 can be inserted and controlled using the system as described above. The surgical opening can also be a natural body orifice, or an opening created after first passing at least a portion of the elongate body through a natural or created opening in the body. In a NOTES procedure, for example, elongate body 12 can be inserted into a patient's stomach through the nose or mouth and then through the esophagus. In this example, once elongate body 12 is within the stomach, a surgical opening can be incised in the stomach wall to provide entry for elongate body 12 into the peritoneal or abdominal cavity. Thus, the system 300 can accurately sense, measure, determined and/or control the shape of elongate body 12 when it is inside a patient, including all or a portion of elongate body 12 beyond the surgical opening, beyond a natural body orifice or both.

As known in the art, an optical sensing fiber can comprise high-density linear arrays of fiber Bragg gratings (FBGs) in the cores of a multicore fiber, as described in "Sensing Shape", *SPIE's OEMagazine*, pp. 18-21 Sep. 2005. There are multiple ways to measure the shape of a fiber, and, thereby, the shape of the instrument with which it is aligned. One method comprises shining a swept wave length laser down the fiber bundle and measuring the reflected light from the fiber bundle. Bends in the fiber bundle change the reflection properties of the FBGs, thereby the FBGs act as local strain gauges. The challenge comes in accurately reading the many FBG arrays to determine the shape of the fiber bundle.

One technique of reading the FBG arrays is the energy leakage technique that strips the cladding along specific regions of the fiber bundle. The bend in relation to the stripped cladding causes the amount of light transmitted through the fiber to increase or decrease in relation to the magnitude and of the bend. One limitation of the technique is that one fiber is required for each direction desired to be measured.

Another technique is cross-coupling of a multi-core fiber, as described in U.S. Pat. No. 6,888,623 titled "Fiber Optic Sensor for Precision 3-D Position Measurement," issued on May 3, 2005. The cross coupling is a function of the shape of the fiber, and by analyzing the energy in each core, it is possible to determine the shape of the fiber.

In wavelength division multiplexing (WDM) Bragg gratings are written at various locations along a multicore fiber with different nominal center wavelengths. Each grating can be addressed independently by choosing the wavelength of light that is shone into the system to be close to the center wavelength of the grating. Strain (i.e., bend) in the fiber near the grating will shift the center wavelength of the grating slightly, which can be measured by the shifts in the reflected spectra. A limitation of this technology is that the number of gratings that can be addressed is limited by the total range of wavelengths that the input light source can be scanned, and the minimum difference in nominal center wavelength, as governed by the amount of shift expected in the wavelengths due to strain in the multicore cable. U.S. Pat. No. 7,317,849 titled "Optical Fiber Sensor and Method," issued on Jan. 8, 2008, further describes this technique.

Optical time domain reflectometry (OTDR) can be used as one solution to the limitations of the WDM technique. This solution allows many simultaneous measurements by writing many gratings at the same nominal center wavelength and using time delay of the reflectance to separate the spatial location of the gratings. The location of reflections in a fiber optic cable is determined by measuring the time-of-flight of light from a launch point into a fiber to receipt of a reflection back to the approximate point of launch. In principle, this technique could be used to isolate the same-center-wavelength gratings, however in practice, the position resolution available by this technique is often coarse.

In another more preferred technique OTDR uses multi-core fiber where all gratings are written at roughly the same nominal wavelength, and the location of the grating is determined in the frequency domain by forming a resonant cavity between the reflection of the gratings and a high reflector at the proximal end of the fiber. This technique requires only one multicore fiber to produce a shape sensor, allows many gratings to be written at the same nominal center wavelength, and permits long fibers. Luna Innovations (www.lunainnovations.com) is an organization that is producing shape sensors built on this technique.

As used herein in, optical shape sensor includes any known optical shape sensor. Details of construction, operation and use of exemplary optical sensors may be found in, without limitation, U.S. Pat. No. 6,376,830 titled "System and Method for Measuring the Transfer Function of a Guided Wave Device," issued on Apr. 23, 2002, U.S. Pat. No. 6,426,496 titled "High Precision Wavelength Monitor for Tunable Laser Systems," issued on Jul. 30, 2002, U.S. Pat. No. 6,856,400 titled "Apparatus and Method for the Complete Characterization of Optical Devices Including Loss, Birefringence and Dispersion Effects" issued on Feb. 15, 2005, U.S. Pat. No. 7,113,659 titled "Efficient Distributed Sensor Fiber," issued on Sep. 26, 2006, and U.S. Pat. No. 7,099,015 titled "Fiber Optic Sensing Device for Measuring a Physical Parameter," issued on Aug. 29, 2006.

When shape sensor 302 comprises an optical shape sensor, the axial orientation of the shape sensor from the proximal end through to the distal end must be aligned relative to the instrument 10, as one method to increase the accuracy of the shape signal produced to correspond to the shape of the elongate body. As described above, working channel 26 runs down the center of instrument 10. In one embodiment, the working channel is moved to an off-center position and the shape sensor is positioned to occupy the space formerly used by the working channel. Alternatively, the shape sensor 302 may be placed off-center in instrument 10. However, all central shape sensor positions may create difficulties in maintaining the axial orientation of shape sensor 302, because as instrument 10 bends the shape sensor can be compressed or stretched and is subject to breaking.

Figure 4:
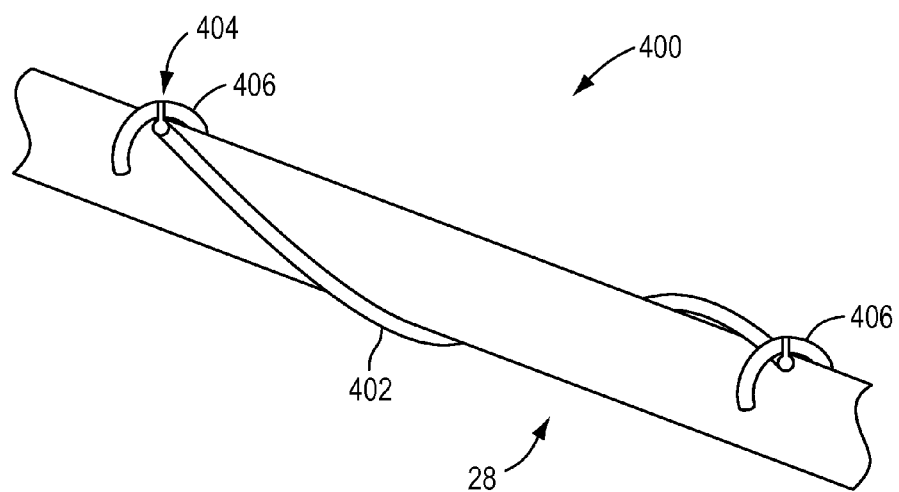
FIG. 4 illustrates an articulating segment having an optical shape sensing fiber along its length in accordance with an embodiment of the present invention.

There are a number of techniques that may be employed to ensure that the shape sensor is positioned to minimize damage and provide accurate signals representing the shape of all or a portion of the elongate body. Referring to FIG. 4, optical shape sensor 402 extends along a portion of the flexible elongate body in a spiral pattern, comprising a single full spiral turn along a single articulating segment 28. In other embodiments, optical shape sensor 402 can extend in a spiral pattern for an integral number of full spiral turns, so long as the axial orientation of the shape sensor from the proximal end through to the distal end of the shape sensor relative to the instrument is maintained, as needed by the specific technical requirements of a particular optical shape sensor. Optical shape sensor can extend in a spiral pattern along only a single articulating segment 28, as shown in FIG. 4, or can extend in a spiral pattern along multiple articulating segments of the elongate body, including along the entire length of the elongate body. In one embodiment, when the shape sensor spirals along multiple articulating segments, the shape sensor spirals for an integral number of full spiral turns for each articulating segment. This maintains the axial orientation along each articulating segment 28, and collectively, therefore, along the elongate body.

The spiraling of optical shape sensor 402 along a portion of the flexible elongate body adds a naturally occurring twist to the optical shape sensor, which disrupts the axial orientation of the shape sensor as it runs along the flexible elongate body. As such, a counter twist must be induced in the optical shape sensor to remove the natural twist caused by the spiraling path along the elongate body and maintain the axial orientation of the shape sensor from the proximal end through to the distal end relative to the elongate body.

As further shown in FIG. 4, optical shape sensor 402 can include at least one indicator 404 on at least the proximal and distal ends of the shape sensor. The indicators 404 can be aligned throughout articulating segment 28 to maintain the axial orientation of the shape sensor proximal end and the shape sensor distal relative to the articulating segment 28. In the embodiment of FIG. 4, indicators 404 are physical indicators, such as tabs extending from the shape sensor. These tabs can be fitted into clips 406, which holds optical shape sensor 402 in place on each end of articulating segment 28 and maintains the axial orientation of the proximal end of the shape sensor relative to the distal end of the shape sensor. In this configuration, however, as described above, if the shape sensor is spiraled along articulating segment, the axial orientation of the shape sensor from the proximal end through to the distal end must still be aligned relative to the articulating segment, such as by inducing a counter twist in the shape sensor. In another embodiment, the physical indicators can be grooves designed to mate with the ends of the articulating segments. In yet another embodiment, indicators 404 can be a visual marker on the shape sensor itself, such as a colored or dotted line that runs the length of the shape sensor, for example. It should be understood that the shape sensor is illustrated on the elongate body for purposes of describing the relative position of the sensor to the elongate body or segment thereof. In some embodiments, the shape sensor is integrated into the elongate body, a sleeve that fits over or is joined to the elongate body or on, within, or about one or more of the articulating segments.

Figure 5:
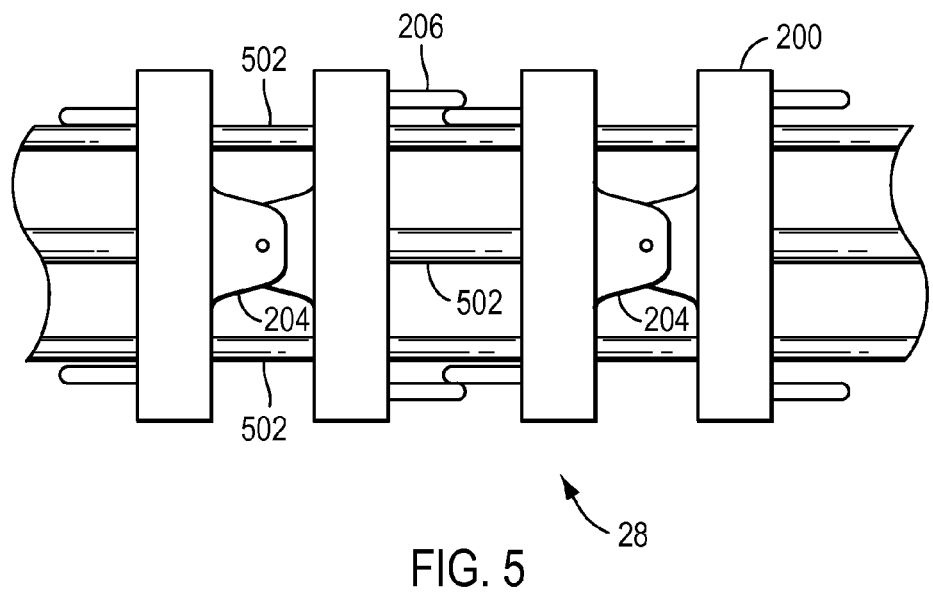
FIG. 5 illustrates an articulating segment utilizing a resistance changing flex sensor to sense the shape of the articulating segment in accordance with an embodiment of the present invention.

Shape sensor 302 described above is not limited to being an optical shape sensor. Referring to FIG. 5, alternatively, resistance changing flexible bands can be implemented in elongate body 12. As known in the art, resistance changing flexible bands change resistance when stretched. One example of resistance changing flexible bands are Stretch Sensors™, available from Images SI Inc. (http://www.imagesco.com/sensors/stretch-sensor.html). As shown in FIG. 5, flexible band sensors 502 can extend along the length of articulating segment 28 of elongate body 12. Pairs of flexible band sensors 502 can run along first and second pairs of hinges 204 and 206 for each bending plane (x-plane and y-plane) of articulating segment 28. In this embodiment, the flexible band sensors will experience a resistance gain and a resistance decrease during articulation. The resistance delta between of the flexible band sensors 502 can be determined or measured and used to determine the shape of each articulating segment 28. Thus, the flexible band sensors 502 can provide a shape signal to controller 30, as described above, corresponding to the shape of at least a portion of elongate body 12.

Figure 6:
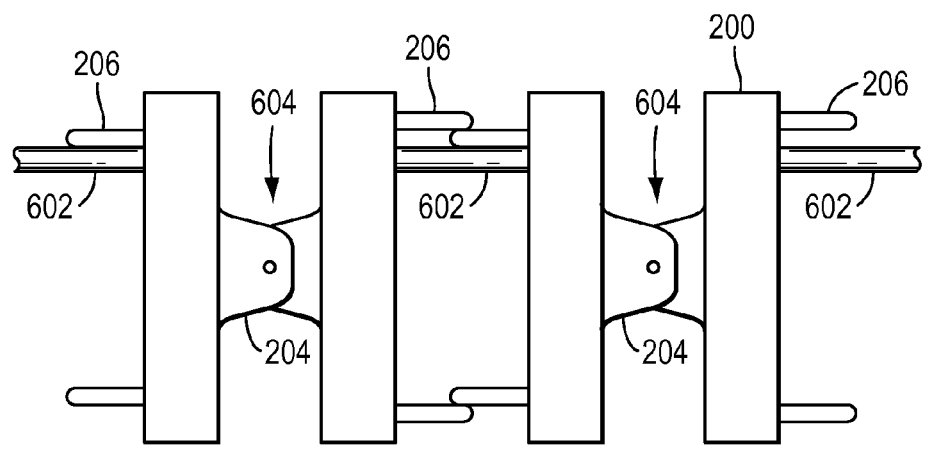
FIG. 6 illustrates an articulating segment utilizing a bend sensor to sense the shape of the articulating segment in accordance with an embodiment of the present invention.

In an alternative embodiment, shape sensor 302 can comprise a plurality of flex sensors, such as those made by FlexPoint (www.flexpoint.com) or SpectraSymbol (www.spectrasymbol.com). As shown in FIG. 6, flex sensors 602 and 604 (flex sensors 604 are provided along hinges 204 but obscured from view in FIG. 6) can be attached to hinges 206 and 204 of each link 200, respectively, to provide a signal to the controller 30 a signal indicative of the angle of articulation. Flex sensors 602 and 604 are flat and bend in one plane, but are essentially not bendable in the orthogonal plane. Thus, in this embodiment, flex sensors 602 and 604 are aligned so the bending plane of each pair of links 200 is approximately parallel with the bending plane of the flex sensor across each hinge. As described above, the flex sensors 602 and 604 can provide a shape signal to controller 30 corresponding to the shape of at least a portion of elongate body 12.

In yet another embodiment, a potentiometer (POT) can be used to measure joint angles as yet another technique for determining the shape of all or a portion of the elongate body. Similar to the embodiments described above, A POT-purchase assembly can be provided at each hinge of the articulating segments 28. In this embodiment, the POT has a wiper that brushes against a carbon film thereby changing the resistance output from the POT. The wiper is attached to a slotted piece, which is fixed on hinges 204 and 206 between adjacent links 200 of articulating segments 28. Articulation of links 200 turns the slotted piece and causes the wiper to brush against the carbon film and change the resistance output of the POT as described. This resistance can be provided as a shape signal to controller 30, as described above, corresponding to the shape of at least a portion of elongate body 12. An alternative to a POT sensor is the use of an optical encoder, as will be appreciated by the skilled artisan.

Another alternative device and technique for shape sensing includes using magnetic sensors, or alternatively sensors that detect variations in magnetic fields generated by a transmitter. Ascension Technology Corporation (http://www.ascension-tech.com/) is developing sensors suited to the purposes described herein. U.S. patent application Ser. No. 11/242,048 titled "DC Magnetic-Based Position and Orientation Monitoring System for Tracking Medical Instruments," filed on Oct. 4, 2005, also discloses this technology. The magnetic sensors can be placed at intervals along elongate body 12, in accordance with an embodiment of the present invention. The spatial orientation of and movements detected by the magnetic sensors may be used to indicate, determine or measure the shape of all or a portion of the elongate body. In the same manner as described above, the magnetic sensors can provide a shape signal to controller 30 corresponding to the shape of at least a portion of elongate body 12.

Figure 7:
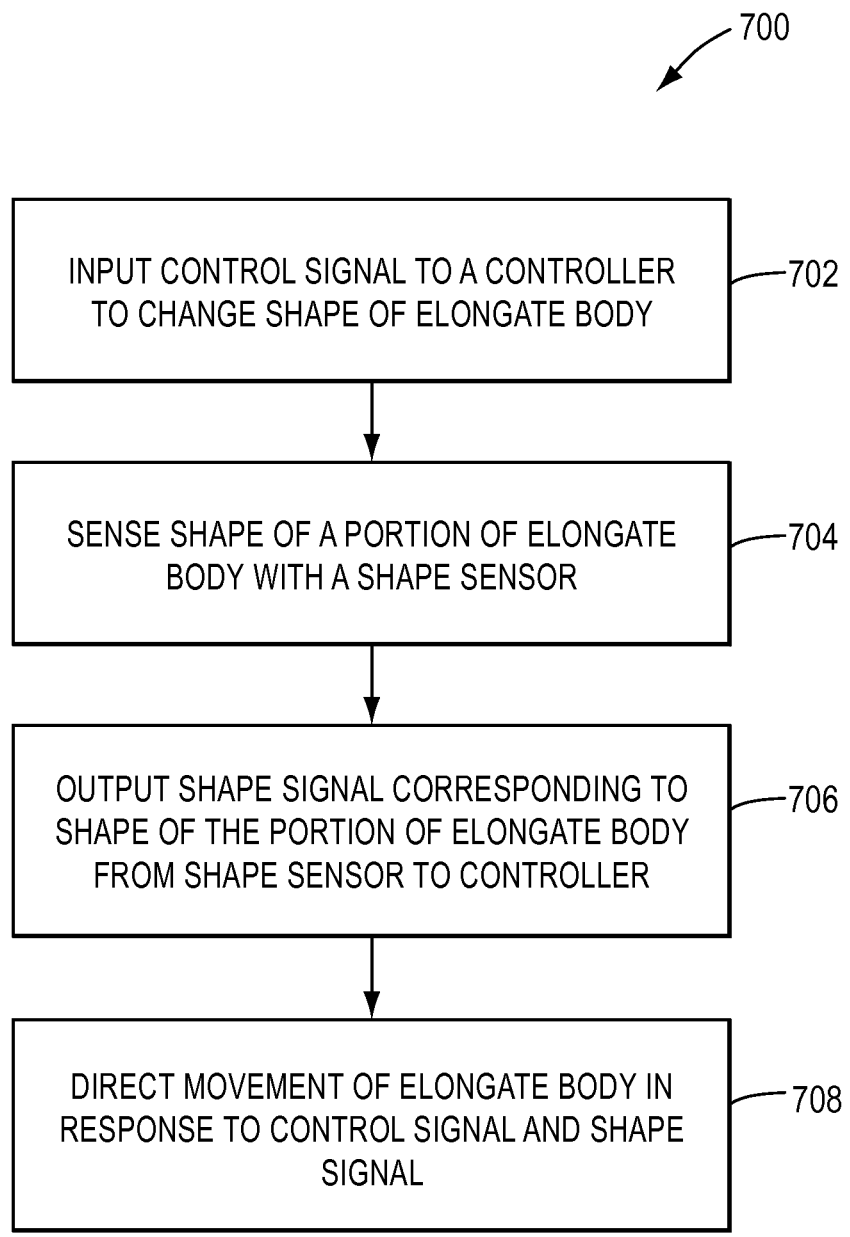
FIG. 7 illustrates a flowchart illustrating steps taken to control an instrument having an elongate body in accordance with an embodiment of the present invention.

FIG. 7 shows a flowchart illustrating an exemplary method of controlling an instrument having an elongate body according to an embodiment of the present invention. Certain details and features have been left out of flowchart 700 that are apparent to a person of ordinary skill in the art. For example, a step may consist of one or more substeps or may involve specialized equipment or materials, as known in the art.

The following description of flowchart 700 includes references to instrument 10 of FIG. 1 and system 300 of FIG. 3, since the method steps in flowchart 700 are implemented utilizing an instrument such as instrument 10. At step 702 of flowchart 700, a control signal is outputted to a controller to change the shape of an instrument having an elongate body. As described above, a user can input a control signal into user input device 42, which can transmit the control signal to controller 30, for example. In one embodiment, controller 30 is in communication with actuator 304 to direct the movement of elongate body 12.

At step 704 of flowchart 700, the shape of at least a portion of the elongate body is sensed with a shape sensor. As described above, shape sensor 302 provides a shape signal corresponding to the shape of at least one of articulating segments 28. In one embodiment, shape sensor 302 runs along the entire length of elongate body 12 to provide a shape signal corresponding to the shape of the entire length of elongate body 12. However, in another embodiment, instrument 10 is inserted into a patient so shape sensor 302 need not run along the entire length of elongate body 12, but rather, only be sufficiently long to indicate the shape of the portion of elongate body 12 inserted into the patient.

At step 706 of flowchart 700, the shape signal corresponding to the shape of the portion of the elongate body is outputted from the shape sensor to the controller. In one embodiment, the outputting step can further include the step outputting the shape signal to a video display to display an output representing the shape of the portion of the elongate body. As described above, system 300 can include a video display configured to receive the shape signal from shape sensor 302 and display an output representing the shape of a portion of elongate body 12. Thus, the user can guide, steer or direct movement or alteration of the shape of the instrument 10 by monitoring the shape of elongate body 12 as it is displayed on the video display.

At step 708 of flowchart 700, the movement of the elongate body is directed in response to the control signal and the shape signal. As described above, controller 30, being in communication with both user input device 42 and shape sensor 302, can direct the movement of at least one of the articulating segments 28 in response to the control signal from user input device 42 and the shape signal from shape sensor 302 to provide a closed-loop feedback control system for controlling instrument 10.

In other embodiments, the method can further include the step of creating a surgical opening in a patient. A surgical opening can be created in a patient into which instrument 10 can be inserted and controlled using the system described above. The surgical opening can also be a natural body orifice, or an opening created after first passing at least a portion of the elongate body through a natural or created opening in the body. Additionally, the method can further include the step of sensing the shape of least a portion of the elongate body beyond the surgical opening, and outputting the shape signal to a video display to display an output representing the shape of the portion of the elongate body beyond the surgical opening.

In addition to sensing the shape of the elongate body, optical sensors can be used to determine the depth of insertion of the elongate body from a particular pre-defined point. This information can also be used to construct the three dimensional shape of the elongate body, as previously described. Two or more shape sensors may be used to determine the depth of insertion of an instrument. Consider a pair of shape sensors. Each sensor is capable of providing x, y, z position within an x, y, z coordinate system. One sensor is placed at a fixed location and is used as a reference location. In one embodiment, the x, y, z tip position of the first sensor is used as the point of reference. The point of reference may be placed at, on or near a natural or surgically created opening in the body. The point of reference sensor may be positioned adjacent a surgically created opening created within the body after entering the body through a natural opening or a surgically created opening. The reference point may be positioned at or near a natural opening even if a surgical opening is created and utilized elsewhere. For example, the reference point may be at or near the mouth when an opening is created in the stomach or at another point in the alimentary canal. Additionally, the reference point opening may be created and the shape sensor and flexible instrument positioned and used in support of NOTES, as described in co-pending patent application Ser. No. 11/522,305 filed Sep. 14, 2006 titled "Methods and Apparatus Useful in Performing Transluminal and Other Procedures." The second sensor is attached to an instrument. The instrument passes near the tip of the first sensor. The x, y, z position of the second instrument is known. Next, compare the x, y, z positions along the instrument until one matches or most nearly corresponds to the x, y, z position of the tip. The x, y, z position on the instrument is then used to determine the position of the instrument relative to the reference point or the depth that the instrument has been inserted beyond the reference point. Additionally, the shape of the second instrument is also known based on information from the second shape sensor. The path, organ or portion of the body traversed relative to the reference point may also be determined using the depth of insertion and the shape of the second shape sensor. Similar techniques may also be used while the instrument is being withdrawn or manipulated.

In an alternative embodiment, the techniques described herein may be used to measure the relative location of a shape sensor with respect to another position sensor that is not a shape sensor. For example, if the anus was placed in a known location on an operating room table, and the shape sensor's base is located in a known location with respect to an operating room table, depth of insertion could be determined entirely using a single shape sensor in the scope, and the second sensor is the "ruler" formed by the known relative locations of the anus and the base of the shape sensor.

It would be possible to discern velocity, acceleration and higher order derivatives from this arrangement as well. Use of multiple sensors could be used to provide redundancy, consistency/error checking, and lower error and lower signal noise through various stochastic estimation techniques (such as extended Kalman filters, Unscented Transform filters, Weiner filtering, H_infinity optimal estimation and the like).

As for additional details pertinent to the various embodiments described herein, materials and manufacturing techniques may be employed as within the level of those with skill in the relevant art. The same may hold true with respect to method-based aspects of the invention in terms of additional acts commonly or logically employed. There are additional system requirements needed to ensure the full integration and proper operation of a shape sensor with the elongate body and associated control system optical shape sensors, for example require a light source and a perfect components to ensure the light source is focused or provided to the optical sensor. These and other conventional components are also included as part of the system 300 as needed by the technical requirements of the particular shape sensor or sensors being used.

Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It is intended that the following claims define the scope of the invention and that methods and structures within the scope of these claims and their equivalents be covered thereby.

What is claimed is:

1. A system for controlling movement of a remotely controlled steerable instrument, the system comprising:
   a surgical instrument comprising a plurality of articulatable segments, the plurality of articulatable segments configured to articulate relative to each other to change a shape of the instrument;
   a shape sensing device comprising a single optical fiber that spirals around the plurality of articulatable segments, the optical fiber being configured to transmit an optical signal indicative of the shape of the plurality of articulatable segments; and
   a controller in signal communication with the optical fiber, wherein the controller is logically coupled to the instrument and is configured to output a control signal to move the instrument in response to receiving at least the optical signal from the optical fiber.

2. The system of claim 1, wherein the optical fiber comprises multiple cores and is configured to vary the optical signal in response to changes in the shape of the instrument.

3. The system of claim 1, wherein the controller is configured to output a control signal to independently control the plurality of articulatable segments to change the shape of the instrument, each of the plurality of articulatable segments further comprises an actuator configured to articulate the plurality of articulatable segments relative to each other.

4. The system of claim 3, wherein the actuators are coupled to the plurality of articulatable segments via tendons.

5. The system of claim 3, further comprising a user input device configured to transmit a control signal to the actuators to change the shape of the plurality of articulating segments.

6. The system of claim 5, wherein the controller is configured to output a signal to the actuators to move at least one of the plurality of articulating segments in response to the control signal from the user input device and the optical signal from the optical fiber.

7. The system of claim 5, wherein the user input device comprises an interactive display configured to display an output representing the shape of at least a portion of the instrument.

8. The system of claim 1:
   wherein the plurality of articulating segments comprises a first segment and a second segment; and
   wherein the controller is configured to calculate a shape of the first segment and a shape of the second segment, based on the optical signal, as the instrument advances or withdraws along a path.

9. The system of claim 1:
   further comprising a user input device having an interface configured to receive a command from a user to change a shape of the instrument to a desired shape; and
   wherein the controller is configured to calculate the shape of the instrument based upon the optical signal from the optical fiber, and the controller is configured to calculate a difference between the desired shape and the shape based upon the optical signal.

10. The system of claim 9, wherein the controller is configured to output the control signal to move the instrument to compensate for the calculated difference between the desired shape and the shape based upon the optical signal.

11. The system of claim 1, further comprising:
   a sensor placed at a fixed reference location, wherein the sensor is in signal communication with the controller and transmits a reference location signal to the controller;
   wherein the optical signal transmitted by the optical fiber represents a position of the instrument; and
   wherein, based upon the optical signal and the reference location signal received by the controller, the controller is configured to calculate a position of the instrument relative to the reference location or to determine a depth the instrument has been inserted beyond the reference location.

12. The system of claim 1, wherein the optical fiber comprises a linear array of high spatial resolution fiber optic bend sensors.

13. The system of claim 1, wherein the optical fiber comprises Bragg gratings.

14. The system of claim 1, wherein the optical fiber extends an integral number of full spiral turns for each of the articulating segments.

15. The system of claim 1, wherein the shape sensing device comprises an orientation indicator at a proximal end and at a distal end of the shape sensing device.

16. The system of claim 15, wherein the orientation indicator comprises a protruding structure that protrudes away from the surgical instrument to indicate an axial orientation of the proximal end of the shape sensing device relative to the distal end of the shape sensing device.

17. The system of claim 15, wherein the orientation indicator comprises a visual marker on the shape sensing device.

18. A system for controlling movement of a remotely controlled steerable instrument, the system comprising:
   a surgical instrument comprising a plurality of articulatable segments, the plurality of articulatable segments configured to articulate relative to each other to change a shape of the instrument;
   a shape sensing device comprising an optical fiber that spirals around the plurality of articulatable segments, the optical fiber including a counter twist in a direction counter to a direction of the spiral of the optical fiber, and also being configured to transmit an optical signal indicative of the shape of the plurality of articulatable segments; and
   a controller in signal communication with the optical fiber, wherein the controller is logically coupled to the instrument and is configured to output a control signal to move the instrument in response to receiving at least the optical signal from the optical fiber.

19. The system of claim 18, wherein the shape sensing device comprises a first orientation indicator at a proximal end and a second orientation indicator at a distal end of the shape sensing device.

20. The system of claim 19, wherein the orientation indicators each comprise a protruding structure that protrudes away from the surgical instrument to indicate an axial orientation of the proximal end of the shape sensing device relative to the distal end of the shape sensing device.

21. A method of controlling movement of a remotely controlled steerable instrument comprising a plurality of articulatable segments, the method comprising:
   receiving an optical signal from a shape sensing device comprising a single optical fiber that spirals around the plurality of articulatable segments, the optical signal being indicative of a shape of the plurality of articulatable segments, the plurality of articulatable segments being configured to articulate relative to each other to change the shape of the instrument; and moving the instrument in response to receiving at least the optical signal from the optical fiber.

22. The method of claim 21, wherein moving the instrument comprises independently moving the plurality of articulatable segments to change the shape of the instrument.

23. The method of claim 21, wherein moving the instrument further comprises moving the instrument based on input at an input device, wherein the input is a user command to move the instrument.

24. The method of claim 21, wherein receiving the optical signal comprises receiving a variable optical signal dependent on changes in the shape of the instrument during the moving.

25. The method of claim 21, further comprising:

receiving from a sensor at a fixed reference location a reference location signal representing a position of the instrument; and based upon the optical signal and the reference location signal, calculating a position of the instrument relative to the reference location or determining a depth the instrument has been inserted beyond the reference location.

* * * * *